(12) United States Patent
Masek

(10) Patent No.: US 10,953,126 B1
(45) Date of Patent: Mar. 23, 2021

(54) EVADE SYSTEM (EXTERNALLY VENTED AEROSOL AND DROPLET EVACUATION SYSTEM)

(71) Applicant: Richard Thomas Masek, San Diego, CA (US)

(72) Inventor: Richard Thomas Masek, San Diego, CA (US)

(*) Notice: Subject to any disclaimer, the term of this patent is extended or adjusted under 35 U.S.C. 154(b) by 0 days.

(21) Appl. No.: 17/100,907

(22) Filed: Nov. 22, 2020

(51) Int. Cl.
| | |
|---|---|
| *A61L 9/20* | (2006.01) |
| *A61C 17/06* | (2006.01) |
| *A61C 17/14* | (2006.01) |
| *A61L 9/12* | (2006.01) |

(52) U.S. Cl.
CPC .... *A61L 9/20* (2013.01); *A61L 9/12* (2013.01); *A61L 2209/12* (2013.01); *A61L 2209/14* (2013.01); *A61L 2209/212* (2013.01)

(58) Field of Classification Search
None
See application file for complete search history.

(56) References Cited

U.S. PATENT DOCUMENTS

| | | | |
|---|---|---|---|
| 5,047,072 A * | 9/1991 | Wertz | B08B 5/04 95/90 |
| 6,045,596 A * | 4/2000 | Holland, Jr. | B01D 46/00 55/385.2 |

* cited by examiner

*Primary Examiner* — Jelitza M Perez

(57) ABSTRACT

The EVADE (Externally Vented Aerosol and Droplet Evacuation) system is designed to treat collected aerosols with ultraviolet radiation and exposure to ozone gas to prevent the spread of COVID or other infectious pathogens. The system uses an externally vented central vacuum system which produces up to 280 CFM of vacuum flow to facilitate collection of potentially contaminated oral aerosols and droplets generated by instrumentation of any type within the medical, dental or any other field which generates said aerosols. The aerosols are collected within a mirrored chamber, reflecting UVC light in all directions and exposing the aerosols to ozone before moving through HEPA particle filtration and out of the environment through the exhaust of a central vacuum system.

1 Claim, 15 Drawing Sheets

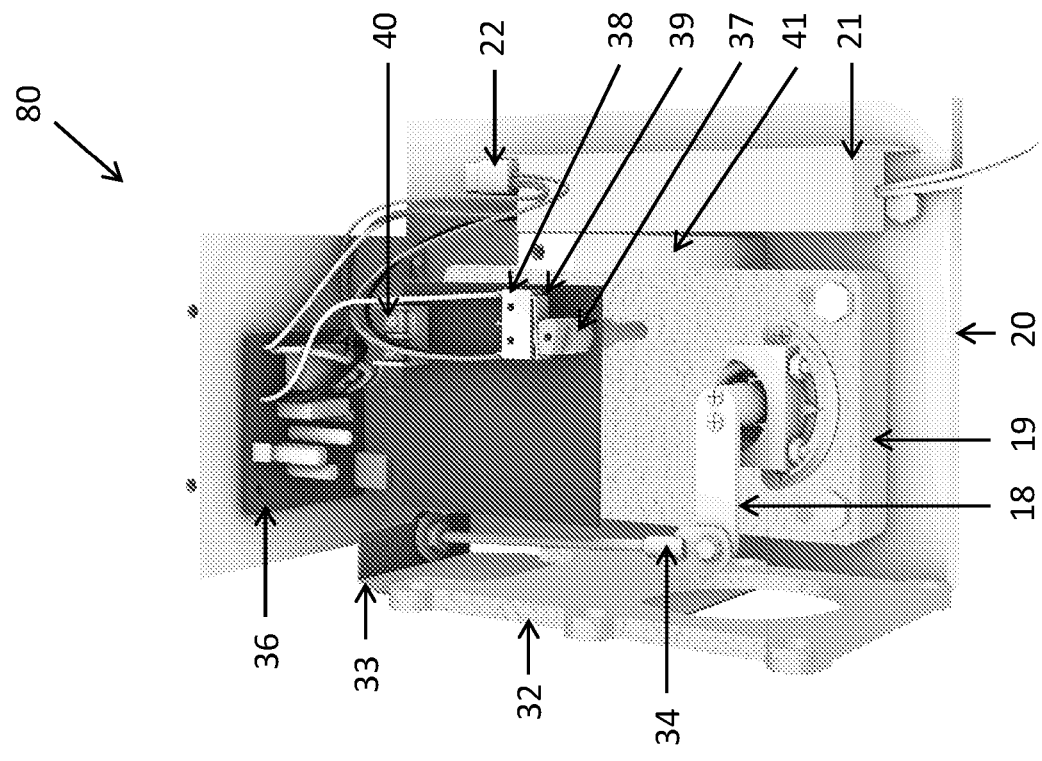
FIG. 6B
FIG. 6
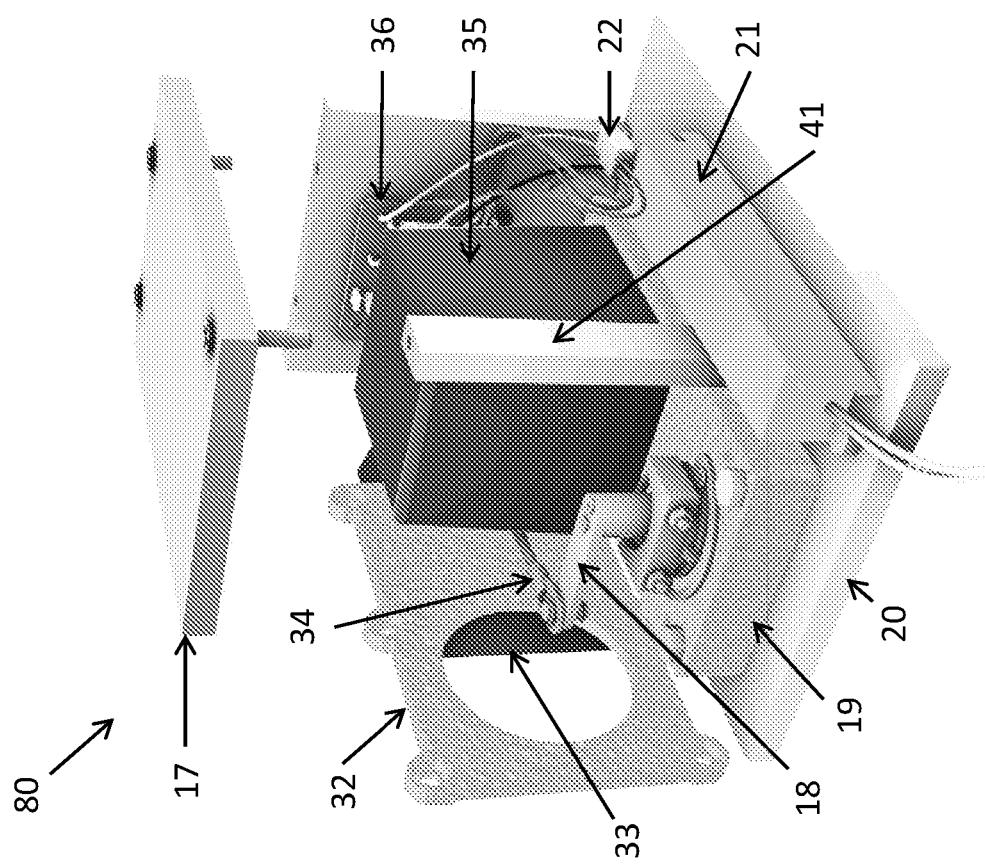
FIG. 6A

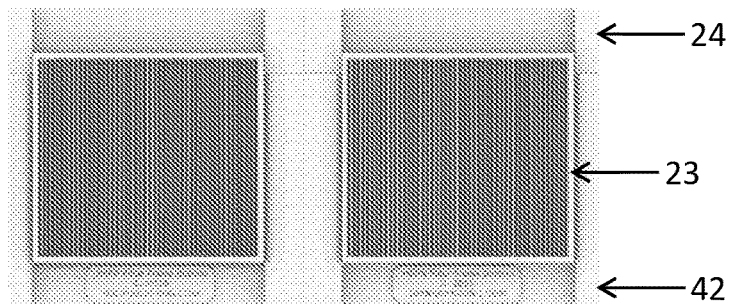
FIG. 7A
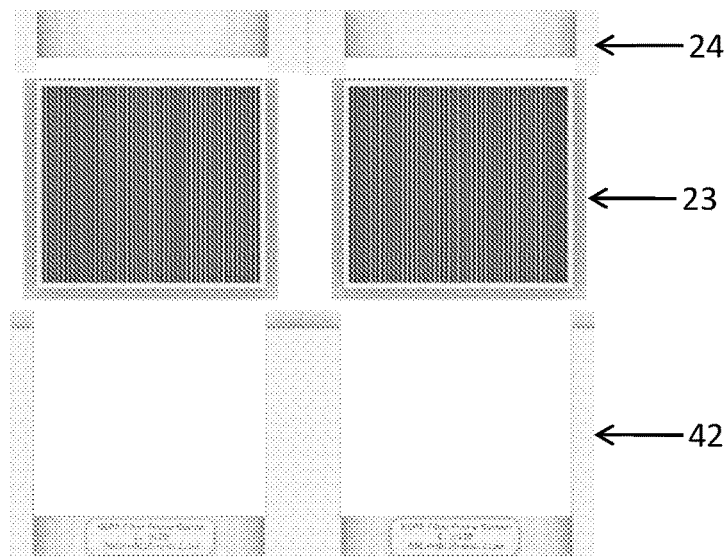
FIG. 7B
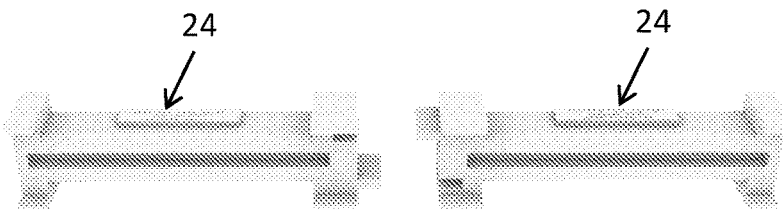
FIG. 7C
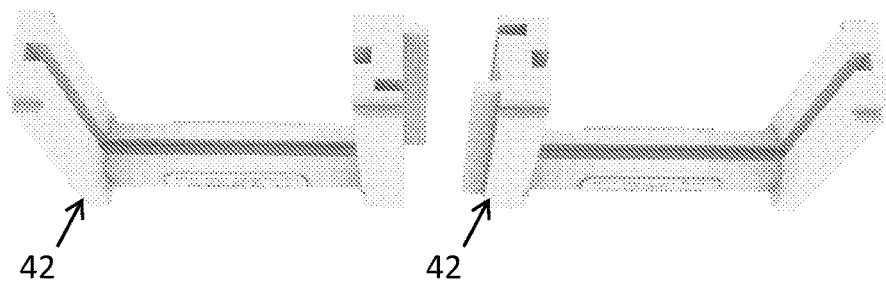
FIG. 7D
FIG. 7

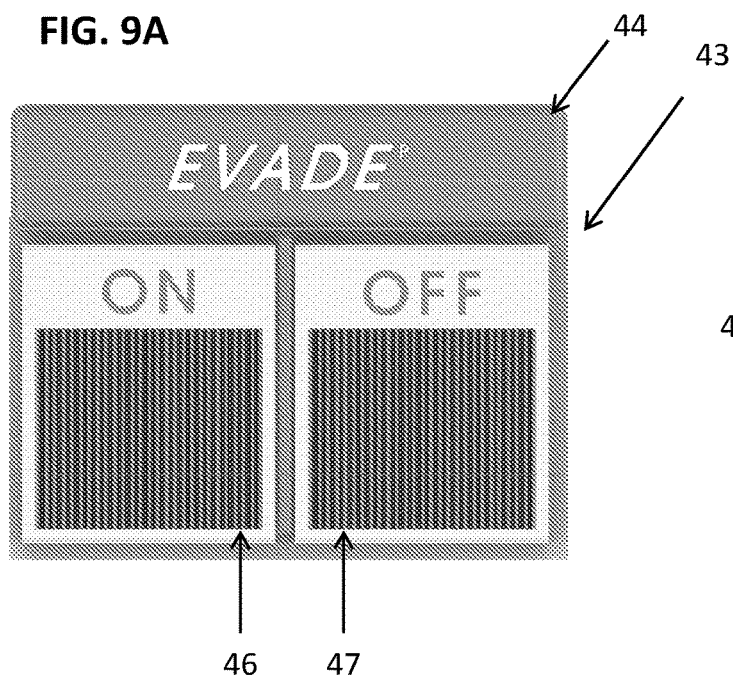
FIG. 9A
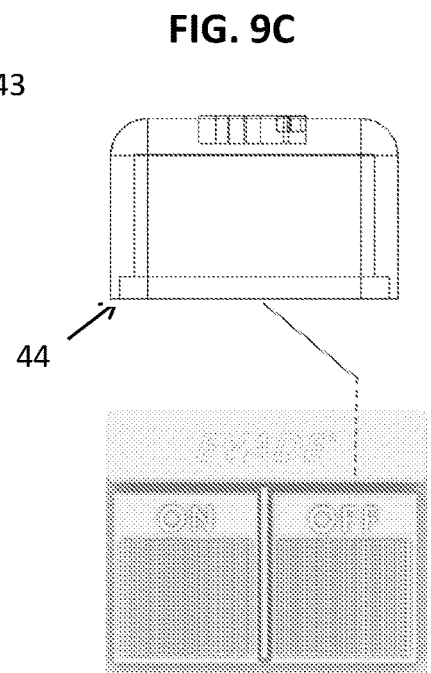
FIG. 9C
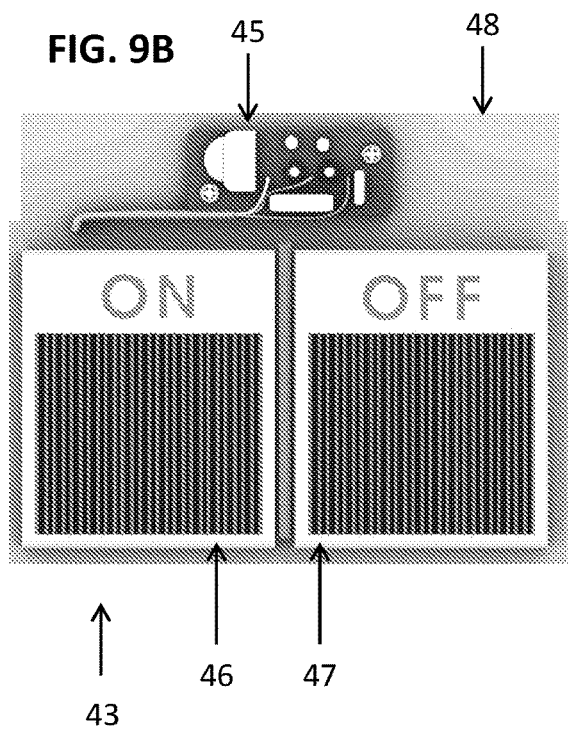
FIG. 9B
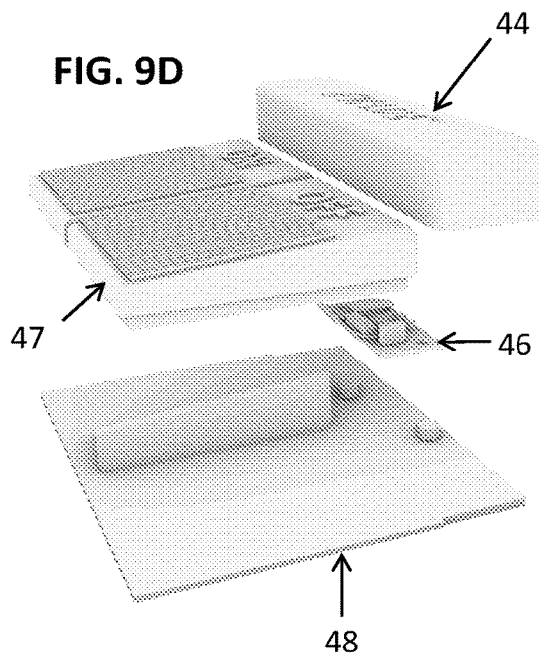
FIG. 9D
FIG. 9

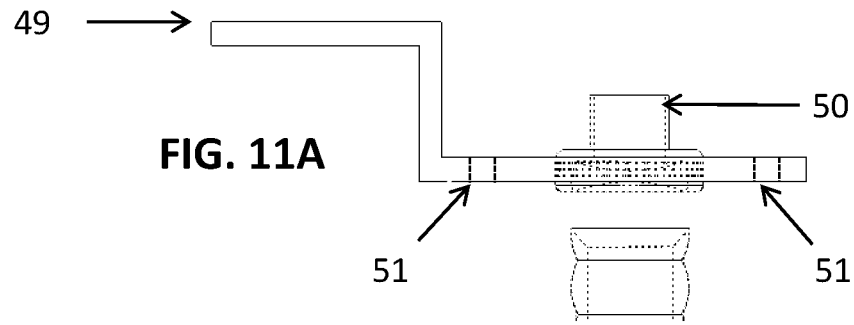
FIG. 11A
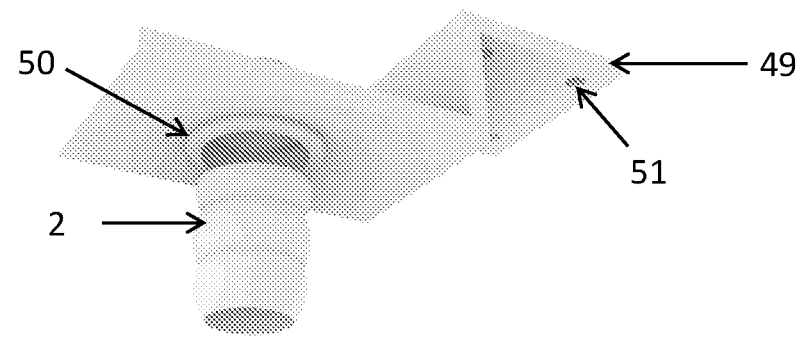
FIG. 11B
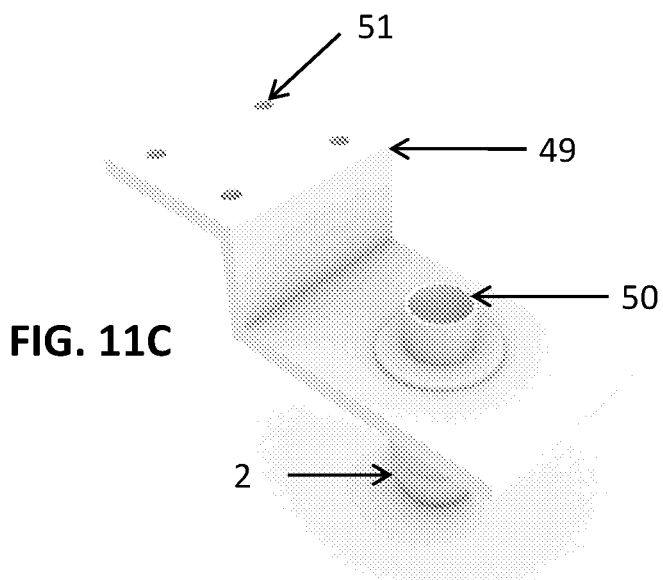
FIG. 11C
FIG. 11

EVADE SYSTEM (EXTERNALLY VENTED AEROSOL AND DROPLET EVACUATION SYSTEM)

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

Many infectious diseases including COVID-19 have a significant potential for spread through orally generated aerosols. This invention is within CPC A61L employing UVC, ozone and HEPA filtration and external discharge of potentially contaminated oral aerosols and droplets generated during patient contact in medical, dental or any such settings which may generate such aerosols. The disclosure relates generally to the handling of potentially infectious oral aerosols, and more particularly, to an improved solution for collection and treating of human aerosols by collection and treatment using ultraviolet radiation, exposure to ozone and removal of said materials from the immediate environment.

Devices exist which use Ultraviolet (UV) and ozone ($O_3$) for air purification and sterilization and are known to have a successful history. Ultraviolet radiation with a wavelength near the absorption peaks of molecules of DNA and proteins of pathogens is effective in their destruction. Ozone is bio destructive, causing bacteria, viruses, fungi and other pathogens to undergo cellular degradation and destruction. Many existing systems additionally rely on HEPA filtration to treat the air which is then recirculated into the environment from which it is collected. Even though UVC and HEPA filtration without ozone is highly effective, re-introducing aerosols treated in this fashion into the occupied environment carries risks if filtration fails or the UVC bulb loses effectiveness or fails. These systems do not include ozone due to the toxic effects which the introduction of ozone into an occupied environment would have upon the respiratory system of humans. The addition of ozone provides a higher rate of destruction of pathogens and external venting of the treated aerosols eliminates the potential for spread of the collected pathogens.

Dental procedures which involve a dental handpiece, ultrasonic scaler and/or 3 way air/water spray syringes generate aerosols and droplets which may contain saliva and other patient fluids. If dispersed in the treatment room, these potentially infectious aerosols and droplets create a hazard to the dental professionals and other patients within the office environment if inhaled or transferred through surface contact within the treatment area.

Other existing solutions which collect and treat generated aerosols produce distracting noise pollution. Airflow can also be a limiting factor in the effectiveness of other systems in collecting the generated aerosols. Other solutions also occupy valuable floor space within the treatment room, and reintroduce the collected air into the treatment room through heated exhaust. Floor space is at a premium in most medical/dental treatment rooms. Making room for an additional piece of equipment can be difficult. Most patients and dental staff also prefer to avoid introducing more ambient noise into the treatment area. The exhaust air from other systems can increase the ambient temperature of the treatment room. If a part of the filtration system fails, such as the UVC bulb, or the filters become clogged, air flow is reduced or contaminants are reintroduced into the treatment environment.

BRIEF SUMMARY OF THE INVENTION

The invention provides a system for collecting, processing and removing aerosols and droplets from the air at the point of aerosol generation in dental, medical or any other environments which generate oral aerosols. The invention provides a solution in which aerosols are exposed to ultraviolet radiation, ozone gas and HEPA filtration. To this extent, the cloud of aerosols is gathered into a closed, mirrored chamber in which it is exposed to ultraviolet radiation and ozone gas in such a manner as to harm (e.g., suppress growth of, reduce an amount of, kill, damage, injure, etc.) any organisms that may be present in the aerosolized volume. The organism(s) may include any combination of various types of organisms, such as bacteria, viruses, fungi or the like. The processed air then passes through HEPA filtration which traps particles greater than 0.3 µm in size, which is smaller than oral pathogenic particles.

The system includes a collection cone with a droplet filter placed near the aerosol source and a flexible hose apparatus for stable positioning. The system is activated using a manual push button switch mounted on the EVADE filtration box or with a remote wireless foot pedal. The system includes a linear actuator which operates a blast gate door to open a path to a central vacuum pipe system. The blast gate allows for multiple units to use the same central vacuum system and only draw vacuum when needed. This prevents vacuum air flow from being compromised by units not in use.

The linear actuator operates a CAM shaft which operates a dual micro-switch apparatus. One of the micro-switches activates the UVC/ozone bulb 15-20 seconds before the second micro-switch activates the vacuum flow. In this manner, the HEPA filters and a mirrored collection chamber are irradiated with UVC light and filled with ozone to disinfect the chamber before the vacuum flow is initiated. To further disinfect the chamber at the termination of the usage episode, the UVC/ozone lamp is left activated for 15-20 seconds as the vacuum powers down and the airflow diminishes.

Treatment of the aerosols is needed even though the collected air is not discharged back into the occupied environment because organisms would have the potential to collect within the vacuum pipe system of the central vacuum collection system. Treatment of the collected aerosols prevents pathogens from breeding and becoming a health hazard. A UVC light is provided within the central vacuum collection canister to further mitigate this issue.

BRIEF DESCRIPTION OF THE SEVERAL VIEWS OF THE DRAWING

Features will be more readily understood from the following detailed descriptions of the various components of the invention and illustrated with the accompanying drawings which depict various aspects of the invention.

FIG. 3A shows the left side view.

FIG. 3B shows the right side view.

FIG. 3C shows the bottom view.

FIG. 3D shows the top view.

FIG. 6 shows the detail of the blast gate module.

FIG. 6A shows the complete blast gate module and alignment of the blast gate protective cover.

FIG. 6B shows the blast gate module with the blast gate protective cover and the actuator cover removed to reveal the actuator CAM and microswitches.

FIG. 7 shows the detail of the HEPA filter module.

FIG. 7A shows the fully assembled HEPA filter module.

FIG. 7B is an exploded diagram of the alignment of the top and bottom filter frame rails and HEPA filters.

FIG. 7C shows the separated top rails of the filter frame assembly.

FIG. 7D shows the separated bottom rails of the filter frame assembly.

FIG. 9 shows the detail of the remote foot pedal assembly.

FIG. 9A shows the fully assembled foot pedal assembly.

FIG. 9B shows the pedal assembly with the transmitter/battery cover removed.

FIG. 9C shows the cross section detail of transmitter/battery cover.

FIG. 9D shows an exploded diagram of the foot pedal assembly.

FIG. 11 shows the detail of the ceiling mounting bracket assembly.

FIG. 11A shows a cross section of the ceiling mounting bracket assembly.

FIG. 11B shows a bottom perspective of the ceiling mounting bracket assembly holes and tubing connector.

FIG. 11C shows a top perspective of the ceiling mounting bracket assembly holes and central vacuum pipe connector.

Figure 1:
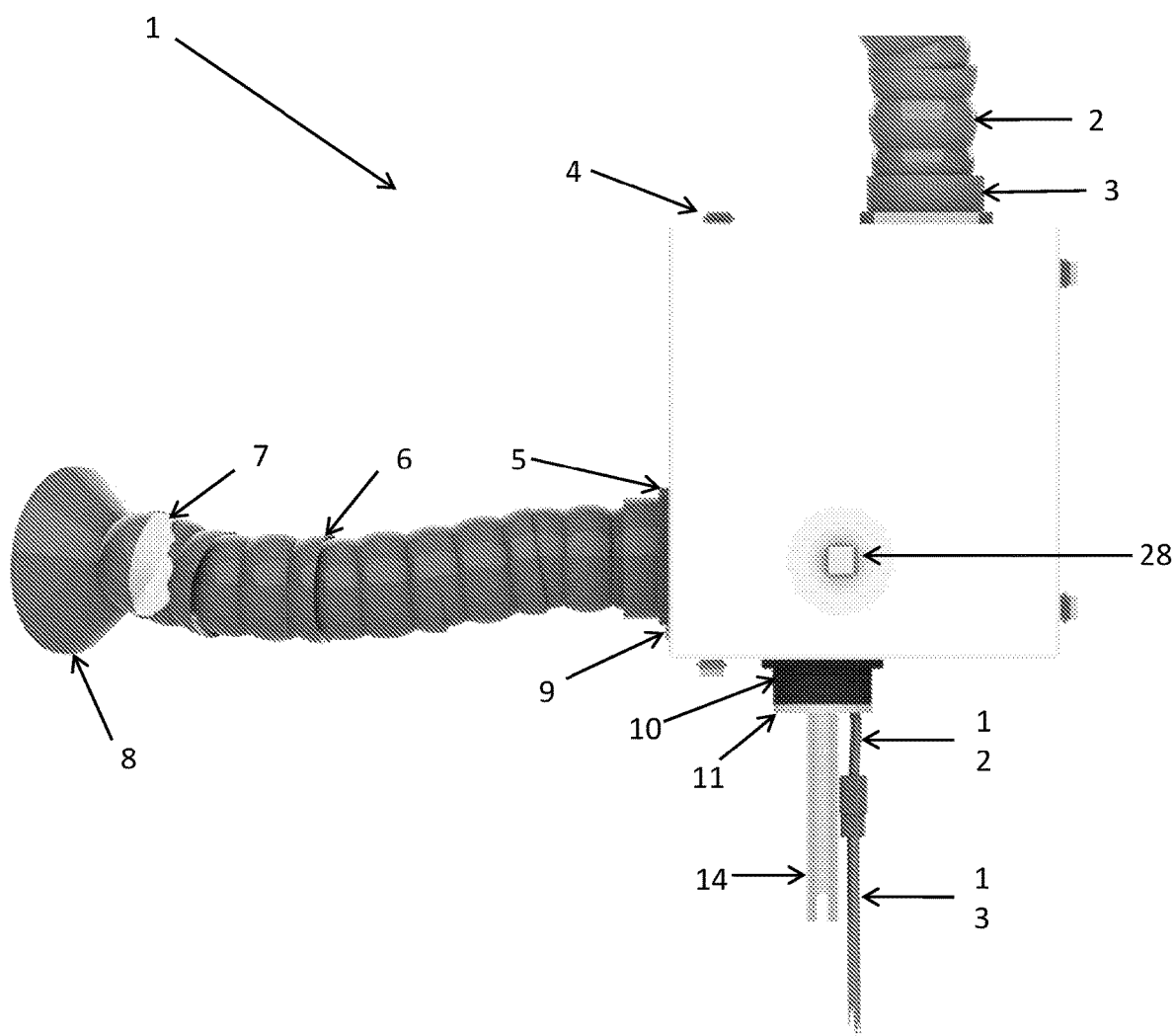
FIG. 1 shows the front view of the assembled EVADE system filtration box.

The drawings are intended to depict typical aspects of the invention. Specific components can be substituted or the layout rearranged depending on the size of the EVADE filtration box and the intended application and therefore should not be considered as limiting the scope of the invention. Like numbering represents like elements between the drawings.

DETAILED DESCRIPTION OF THE INVENTION

The invention includes a collection cone 8 with a droplet filter 7 placed near the aerosol source and a flexible hose apparatus 6 for stable positioning. The hose is connected to the EVADE filtration box using a snap connect fitting 5 to enable replacement of any parts should they become damaged in use. The collection hose may be covered with a disposable plastic barrier sleeve to aid in disinfection between uses. The potentially contaminated aerosols and droplets are drawn into the mirrored chamber 25 housing a UVC light source 27 which also generates ozone. The UVC light reflects throughout the chamber and the generated ozone mixes with the aerosols passing through.

The disinfected aerosols then pass through two replaceable HEPA filters 23. The processed aerosols pass into the central vacuum system piping which is connected by a flexible hose 2 using a snap connect fitting 3 to enable replacement of any parts should they become damaged in use. Depending upon the installation, the EVADE filtration box can be connected directly to the rigid vacuum pipe system. The processed aerosols are again exposed to UVC/ozone in the central vacuum system collection canister 54 prior to being ejected to the outside atmosphere via the exhaust of the central vacuum system 58.

The EVADE System (Externally Vented Aerosol and Droplet Evacuation) captures aerosols and droplets by means of a flexible tubing 6 and collection cone 8 positioned within millimeters of the patient's mouth during procedures which generate potentially infectious aerosols and droplets. To avoid reintroduction into the treatment area, the contaminated incoming aerosol material is exposed to a UVC/Ozone germicidal lamp 27 and HEPA filters 23 trapping at least 99.97% of airborne particles 0.3 µm in diameter or larger to provide decontamination. The vacuum tubing is connected to the filtration box 1 and the treated aerosols are removed from the environment through a central vacuum system 52. A remotely controlled, electrically operated vacuum valve 32 opens the vacuum connection which ejects the air outside the facility and away from the treatment environment.

The EVADE system's UVC plus Ozone allows for higher level of disinfection before air is discharged into the outside environment. There is no footprint to take up valuable floor space. The vacuum airflow is considerably higher at over 280 CFM than other solutions with very low ambient noise in the treatment room and no heat generation. Positioning is simple from the chair mounted filtration box 1 and tubing 6 and there is no reintroduction of treated air into the office environment.

Installation of the EVADE filtration box as close as possible to the source is preferable to lessen the length of potentially contaminated collection hose 6 prior to filtration. The filtration box may be installed at a remote location. For dental applications, the filtration box may be installed at the patient chair 61 and fixed to the equipment mounting post 50 as illustrated in the following figures.

DETAILED DESCRIPTION OF THE DRAWINGS

Turning to the drawings, the illustrative aspects of the invention are provided to describe the specific components of the EVADE system.

FIG. 1 shows the front view of the system EVADE filtration box 1. The unit may be constructed from various materials which are preferably resistant to degradation from exposure to UVC. The embodiment demonstrated here is manufactured utilizing UVC resistive ⅜" opaque white Plexiglas with five sides bonded for an airtight seal. The central vacuum system is connected through a flexible vacuum tube 2 which is connected to the box by means of a resin based bulkhead mounted vacuum tube connector 3 attached with four stainless steel screws and locknuts. Four stainless steel hasp clasps 4 are each attached to the filtration box 1 and opaque white Plexiglas removable back 15 with self-threading stainless steel screws hold the removable back 15 of the EVADE filtration box 1.

The resin based aerosol inlet bulkhead connector 5 attached with four stainless steel screws and locknuts retains the Acetyl flexible aerosol collection tube 6 which is fitted with a disposable aerosol collection filter 7 and the Acetyl aerosol collection cone 8. The system is activated by depressing the momentary contact on/off switch 9 mounted through a hole drilled in the left side of filtration box 1 or the remote foot pedal 43. In this embodiment the EVADE filtration box 1 is mounted to a dental chair by way of an ABS plastic post mount sleeve 10 attached with four stainless steel screws and locknuts. The PVC anti-rotational tube sleeve 11 supports and stabilizes the stainless steel anti-rotational tube 14 and serves as a wire guide for the power/vacuum cable and connector 12 which is attached to the dental unit power/vacuum switch cable and connector 13. The clear plastic UVC/ozone indicator 28 is mounted through a hole drilled into the front of EVADE filtration box 1 and illuminates when the UVC/ozone bulb lights serving as an on/off indicator as well as verification that the UVC bulb is functional.

Figure 2:
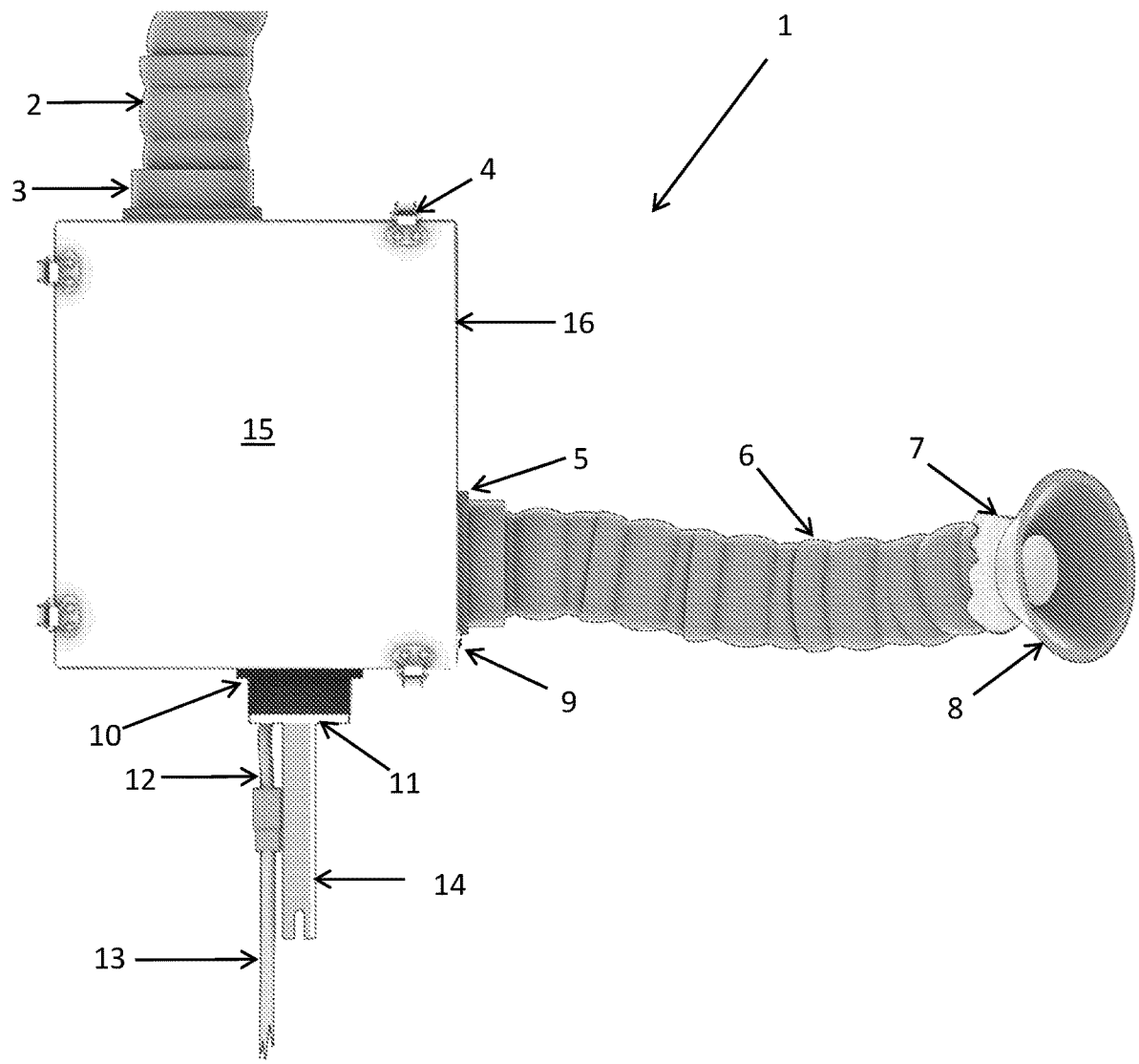
FIG. 2 shows the back view of the assembled EVADE system filtration box.

FIG. 2 is a back view of the EVADE filtration box 1. The central vacuum system is connected through the flexible vacuum tube 2 which is connected to the box by means of the bulkhead mounted vacuum tube connector 3. Four hasp clasps 4 hold the removable back 15 and an airtight seal is accomplished with UV resistant gasket 16. The aerosol inlet bulkhead connector 5 attaches the flexible aerosol collection tube 6 which is fitted with a disposable aerosol collection filter 7 and the aerosol collection cone 8.

The system is activated by depressing the momentary contact on/off switch 9 or the remote foot pedal 43. The EVADE filtration box 1 is mounted to a dental chair by way of the post mount sleeve 10. The anti-rotational tube sleeve 11 supports and stabilizes the anti-rotational tube 14 and serves as a wire guide for the power/vacuum cable and connector 12 which attaches to the dental unit power/vacuum switch cable and connector 13.

Figure 3:
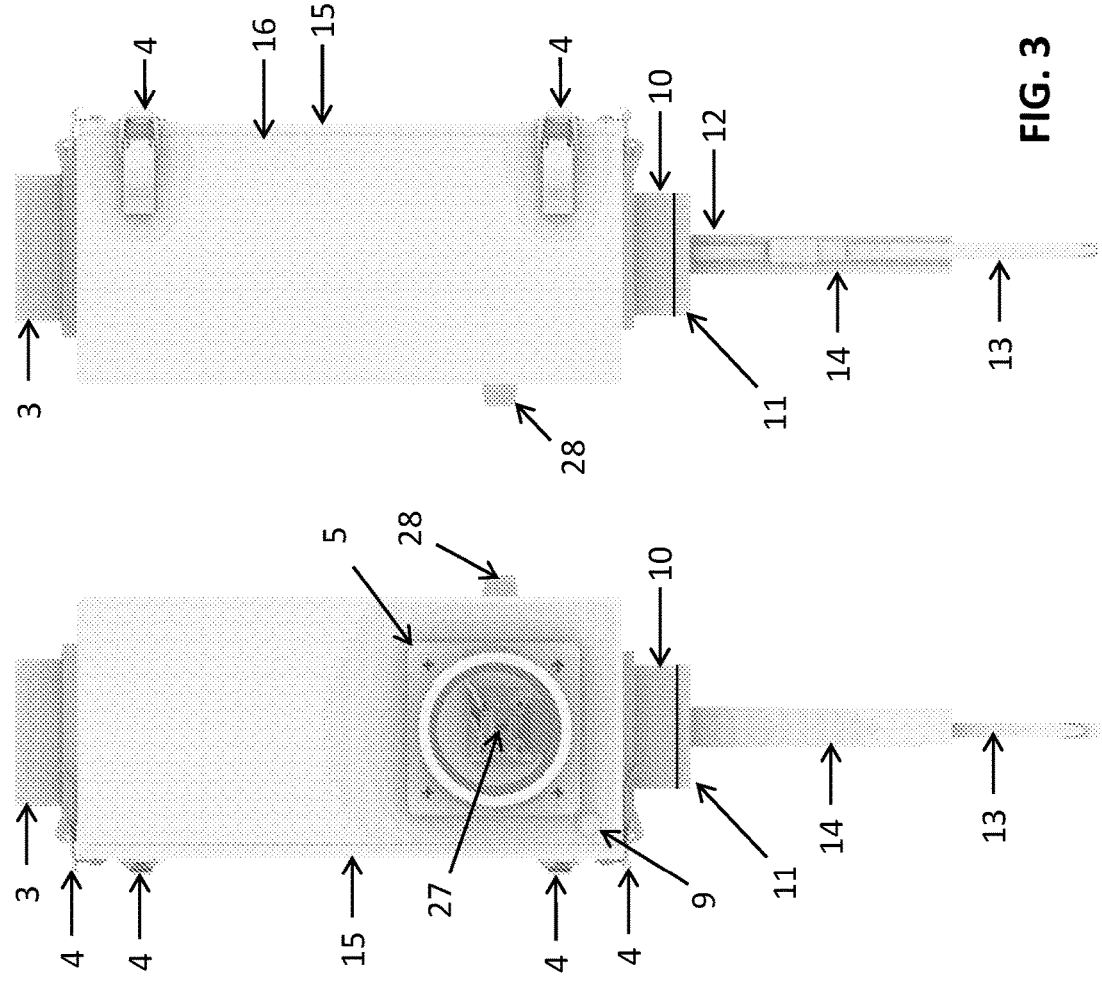
FIG. 3 shows the four sides of the assembled EVADE system filtration box.

FIG. 3 identifies the remaining four sides of the EVADE filtration box. The bulkhead vacuum tube connector 3 detailed in FIG. 3A, FIG. 3B and FIG. 3C is mounted on the top and in the top view reveals one of the HEPA filters 23 in FIG. 3D. Four hasp clasps 4 hold the removable back 15 with an airtight seal accomplished with gasket 16. In FIG. 3A the UVC/Ozone germicidal bulb 27 which illuminates the UVC/ozone lamp indicator 28 when activated is visible through the aerosol inlet bulkhead connector 5. The system is activated by depressing the momentary contact on/off switch 9 as shown in FIG. 3A and FIG. 3D. FIG. 3A and FIG. 3B show the post mount sleeve 10 which houses the anti-rotational tube sleeve 11 which supports and stabilizes the anti-rotational tube 14 and serves as a wire guide for the power/vacuum cable and connector 12 which attaches to the dental unit power/vacuum switch cable and connector 13.

Figure 4:
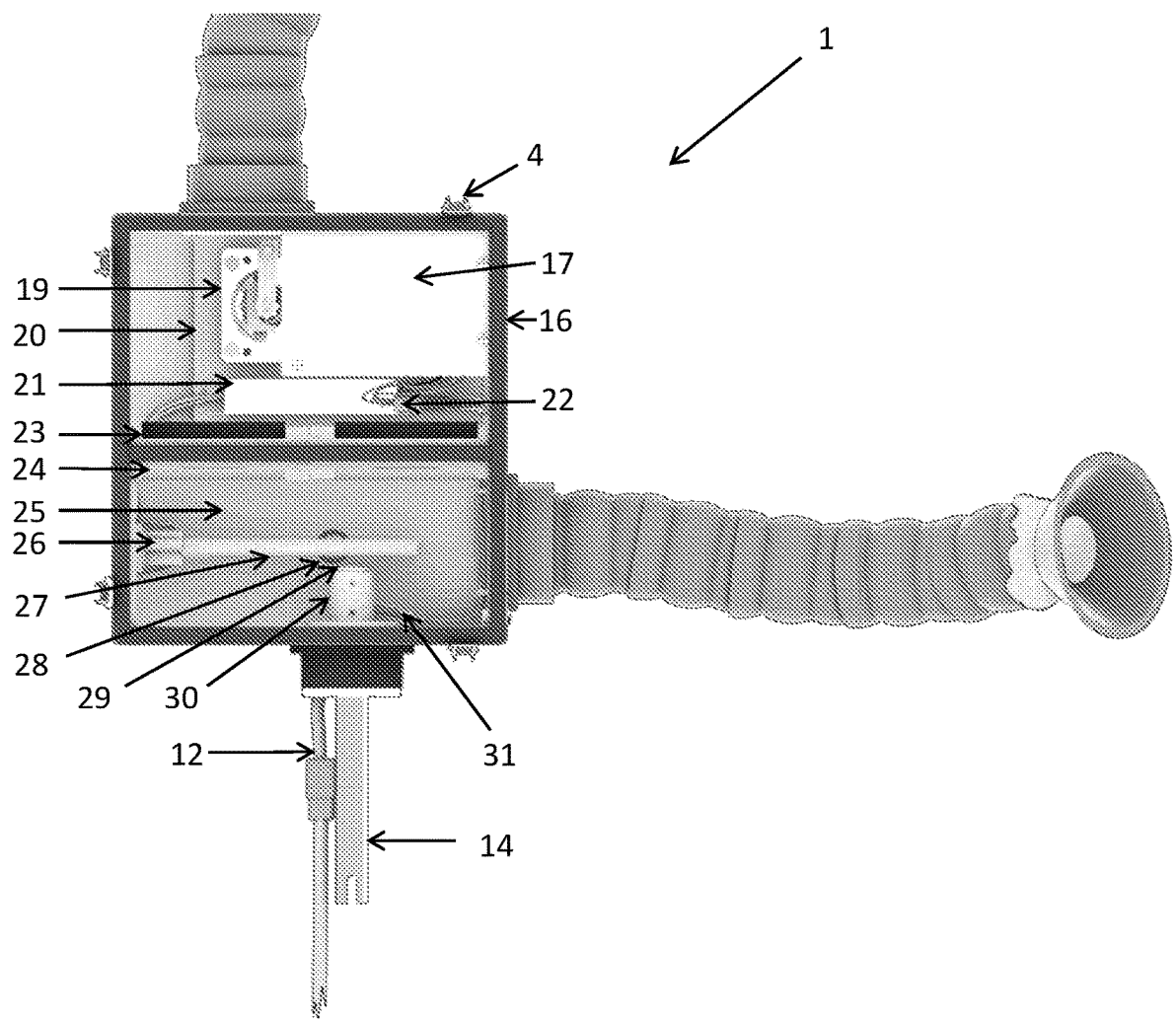
FIG. 4 shows the back view of the EVADE system filtration box with the back lid removed to reveal the internal components.

FIG. 4 shows the EVADE filtration box 1 with the back cover removed to reveal some of the internal components. The self-adhesive gasket 16 is affixed to the perimeter of the EVADE filtration box 1 and the top of the HEPA filter frame module 24 to create an airtight seal when the back cover is secured with the four hasp clasps 4. The actuator/remote protective cover 17 secured with three stainless steel screws protects service personnel from exposure to wires and connections when the HEPA filters 23 require replacement. The blast gate module platform 20 with the blast gate module power/vacuum switch cable and connector 22 is held in place with four self-threading stainless steel screws and holds the linear actuator 19 (in this embodiment the actuator is a Neptronics BT 160 National Environmental Products Ltd. Montreal, Canada). The UVC/ozone lamp ballast 21 is secured with two self-threading stainless steel screws.

The mirrored UVC reflector chamber 25 houses the UVC/ozone lamp socket 26 secured with four stainless steel screws and locknuts which connects to the UVC/Ozone germicidal bulb 27 that illuminates the UVC/ozone lamp indicator 28 when activated. The resin based flange cap 29 seals the stainless steel anti-rotational tube flange 30 which is secured to the bottom of the EVADE filtration box 1 with three stainless steel screws and locknuts. A UVC/ozone resistant sleeve 31 protects the power cable 12 from degradation by UVC and ozone exposure.

Figure 5:
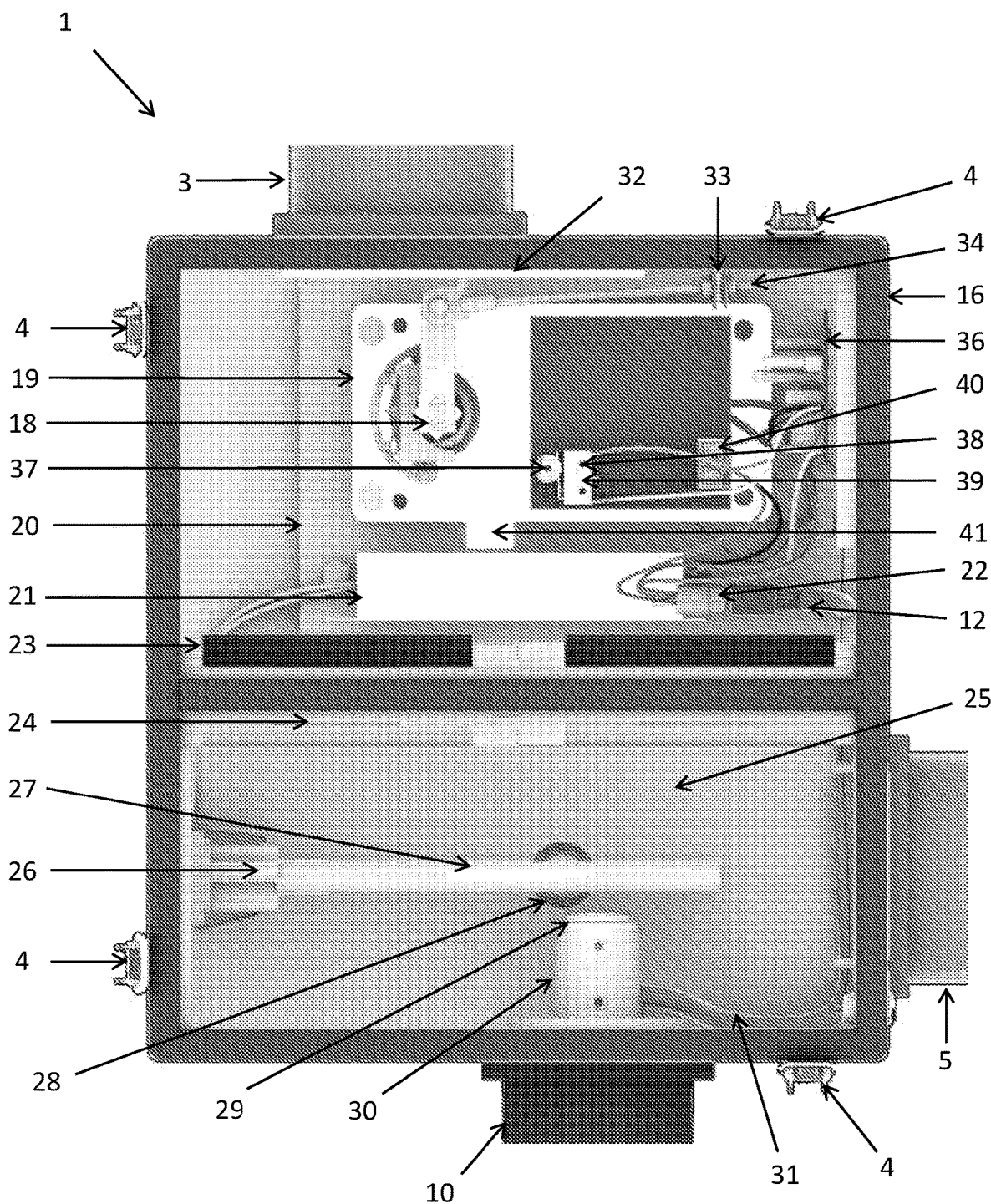
FIG. 5 shows the back view of the EVADE system filtration box with the back lid, blast gate module protective cover and actuator cover removed.

FIG. 5 identifies the components of the blast gate module platform 20 with the actuator/remote protective cover 17 and the actuator cover 35 removed. The actuator/remote protective cover 17 is secured to the actuator/remote cover support 41 and the blast gate module platform 20. When the remote control board 36 is triggered and the system is activated the aluminum blast gate actuator arm 18 begins to open the aluminum blast gate door 33 housed within the aluminum blast gate frame 32 via the stainless steel blast gate adjustable linkage connector 34 making a patent connection to the bulkhead mounted vacuum tube connector 3. Rotation of the micro-switch control CAM 37 also begins which activates the UVC/ozone lamp micro-switch 38 to irradiate the UVC reflector chamber 25 prior to the activation of the vacuum micro-switch 39. This prior activation allows the UVC/ozone to treat any debris remaining on the HEPA filters 23 from previous usages before vacuum beings to flow.

FIG. 6 shows two views of the blast gate module 80. FIG. 6A identifies the components of the blast gate module 80 with the actuator/remote cover 17 removed from the actuator/remote cover support 41 and the blast gate module platform 20. FIG. 6B demonstrates the linear actuator 19 with the actuator cover 35 removed to expose the micro-switch control CAM 37 the UVC lamp micro-switch 38 and central vacuum micro-switch 39. When activated, the linear actuator 19 drives the blast gate actuator arm 18 attached to the blast gate adjustable linkage connector 34 which moves the blast gate door 33 to an open position within the blast gate frame 32 to allow vacuum flow.

The blast gate module power/vacuum switch cable and connector 22 brings power to the remote control board 36. Upon depression of the remote foot pedal 43 or the manual on/off switch 9 which is hard wired to the remote control board 36 power is supplied to the actuator power terminal block 40 and the micro-switch control CAM 37 begins to rotate activating the UVC lamp ballast 21 through the UVC lamp micro-switch 38. The CAM also activates the central vacuum micro-switch 39 several seconds later to begin vacuum flow.

FIG. 7 identifies the components of the assembled HEPA filter assembly FIG. 7A consisting of interchangeable right and left filter frame bottom sections 42 and right and interchangeable left filter frame top sections 24 and two removable HEPA filters 23 which slide into the slotted channels to create an airtight seal. The filter frame assembly is depicted in four sections. The right and left sides interlock to form a complete bottom and a complete top section. The exploded FIG. 7B drawing shows the alignment of the components and FIG. 7 C and FIG. 7D demonstrate the top, bottom, and side channels that retain and seal the HEPA filters 23 as well as the dovetail joints that serve to join the sections together with an airtight seal. This embodiment uses UV resistant resin materials for the filter frame and other embodiments may use other materials. Additional configurations are possible in which the entire bottom section is a single piece and the entire top section is a single piece that houses a HEPA filter of the desired size. This configuration uses two separate HEPA filters and other configurations may use a single filter.

Figure 8:
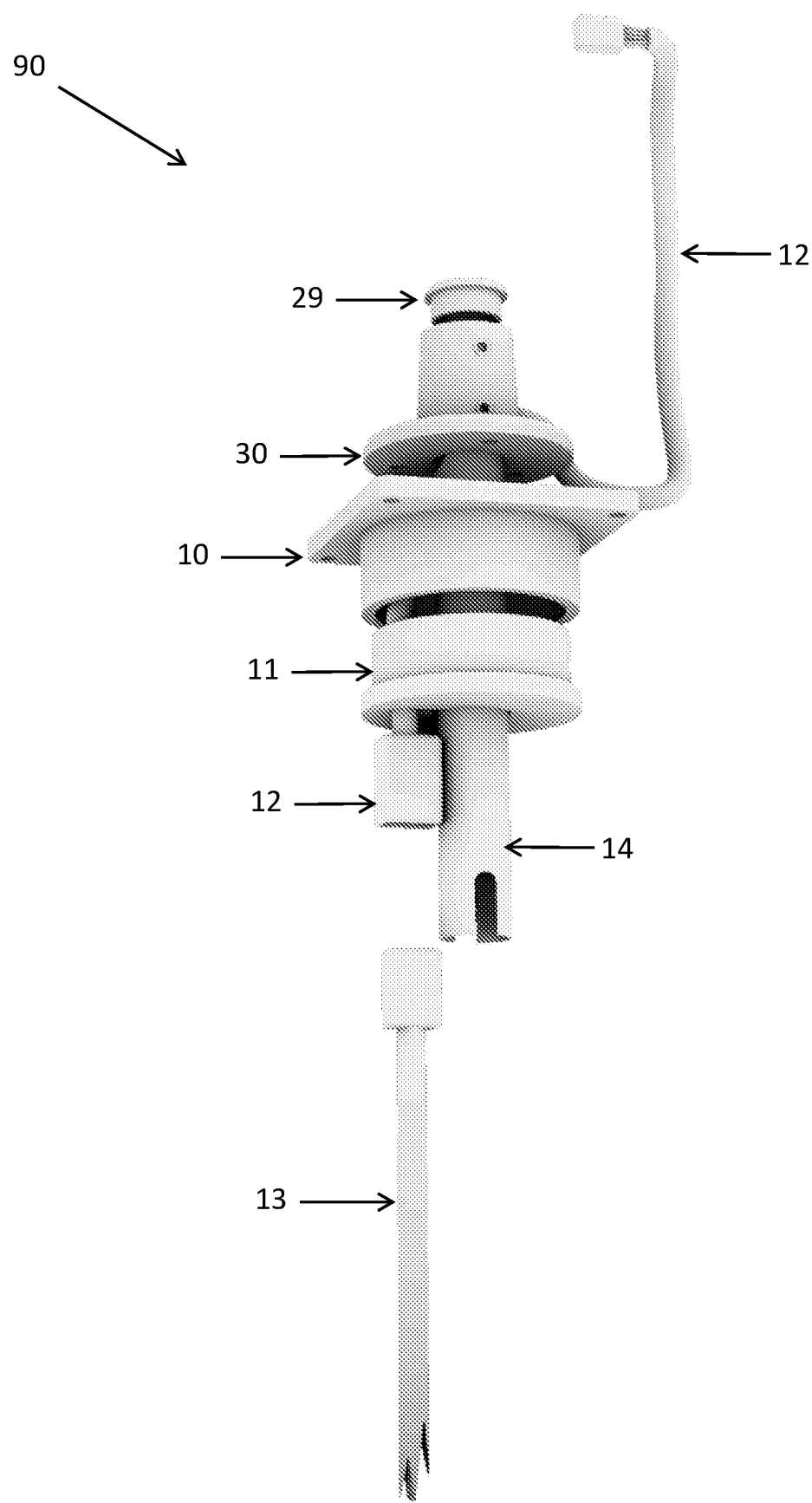
FIG. 8 shows the detail of the dental chair post mounting assembly.

FIG. 8 is a detail of the components which make up the post mounting assembly 90 used to attach the filter box to a dental chair. Sleeve 10 is fixed to the bottom of the EVADE filter box and slides into the existing dental chair post assembly. The anti-rotational tube flange 30 is fixed to the inside of the filter box and sealed with the flange cap 29. The anti-rotational tube sleeve 11 supports and stabilizes the anti-rotational tube 14 and serves as a wire guide for the power/vacuum cable and connector 12 which attaches to the dental unit power/vacuum switch cable and connector 13. The anti-rotational tube 14 has a U-channel at its base to engage a cross member pin inside the dental chair post for anti-rotation stability. This secures the EVADE filter box fixing it in place and prevents it from rotating while allowing the dental delivery arm below to rotate freely.

FIG. 9 identifies the components of the remote foot pedal assembly 43. FIG. 9A shows the complete assembly and FIG. 9B shows the remote transmitter/battery compartment cover 44 removed to reveal the remote transmitter and battery assembly 45 mounted on the foot pedal base 48. The ON foot pedal 46 and the OFF foot pedal 47 activate the remote transmitter board 45 to turn the system on and off. A cross section of the remote transmitter/battery compartment cover 44 is shown in FIG. 9C and an exploded view of the assembly is shown in FIG. 9D.

Figure 10:
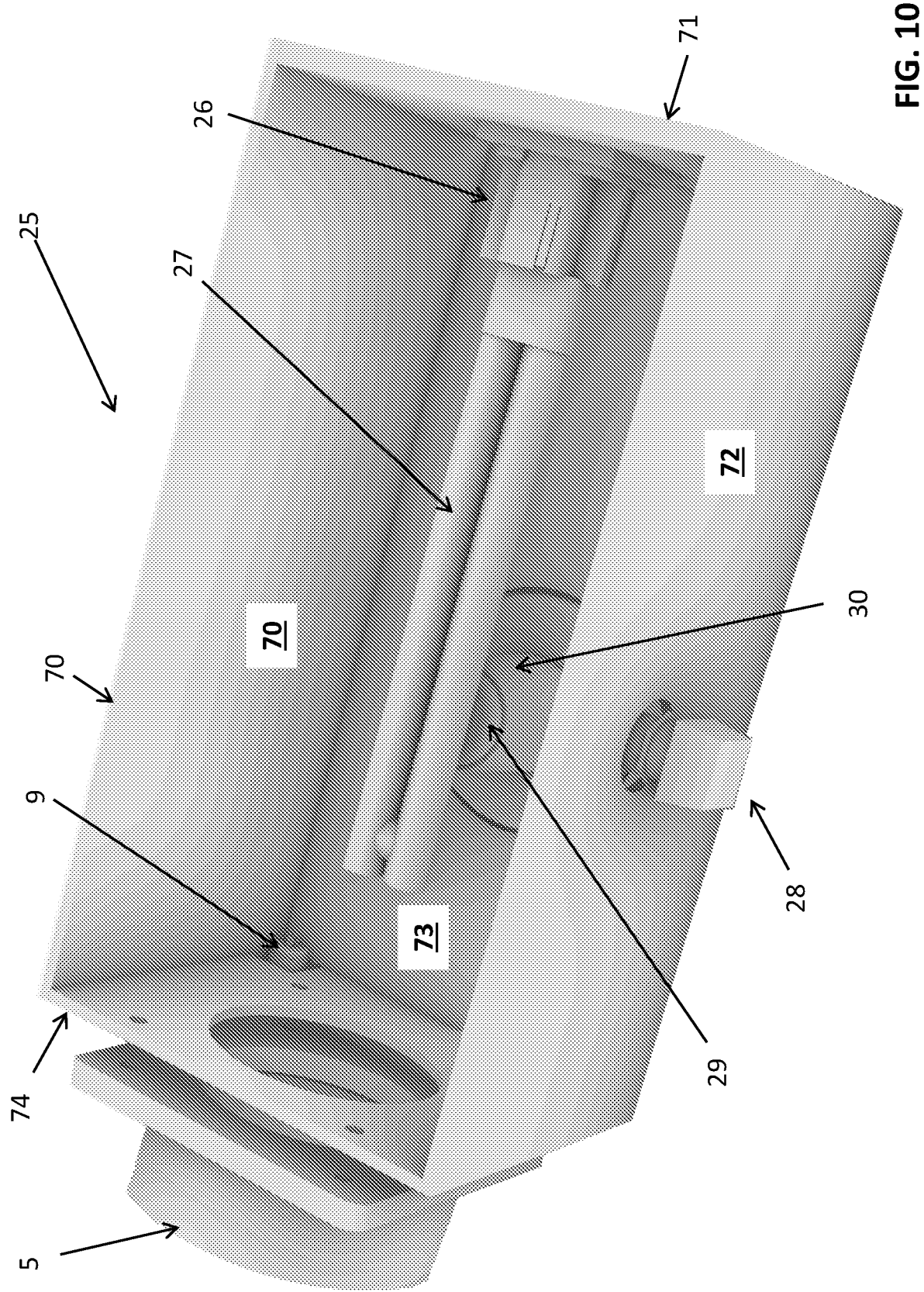
FIG. 10 shows the detail of the UVC mirror chamber.

FIG. 10 identifies the components of the UVC mirror chamber 25 shown in FIG. 4 and FIG. 5. In this embodiment five walls are lined with UV resistive Plexiglas mirror to reflect UVC light generated by the UVC/Ozone germicidal bulb 27 supported by the UVC lamp socket 26 which is attached to mirror section 71 adhesively attached to the right side of the EVADE filtration box 1. Mirror side 72 is secured to the inside front of the EVADE filtration box 1 held by the UVC/ozone lamp indicator 28 while mirror section 74 is attached to the left side and secured by the aerosol inlet bulkhead connector 5 screws and the manual on/off switch 9. Mirror section 73 is held in place by the anti-rotational tube flange 30 and screws which is sealed with the flange cap 29. Mirror section 70 is adhesively affixed to the inside of the removable back 15.

FIG. 11 identifies the aluminum ceiling vacuum Z bracket 48. The cross section shown in FIG. 11A shows the alignment of the ceiling vacuum pipe adapter 49 which allows connection between the in wall vacuum pipe and the flexible vacuum tube 2 and four mounting holes 50. The bottom perspective view in FIG. 11B shows the attachment of the flexible vacuum tube 2 to the ceiling vacuum pipe adapter 49 and the mounting holes 50. The top perspective view in FIG. 11C shows the ceiling vacuum pipe adapter 49 and the mounting holes 50.

Figure 12:
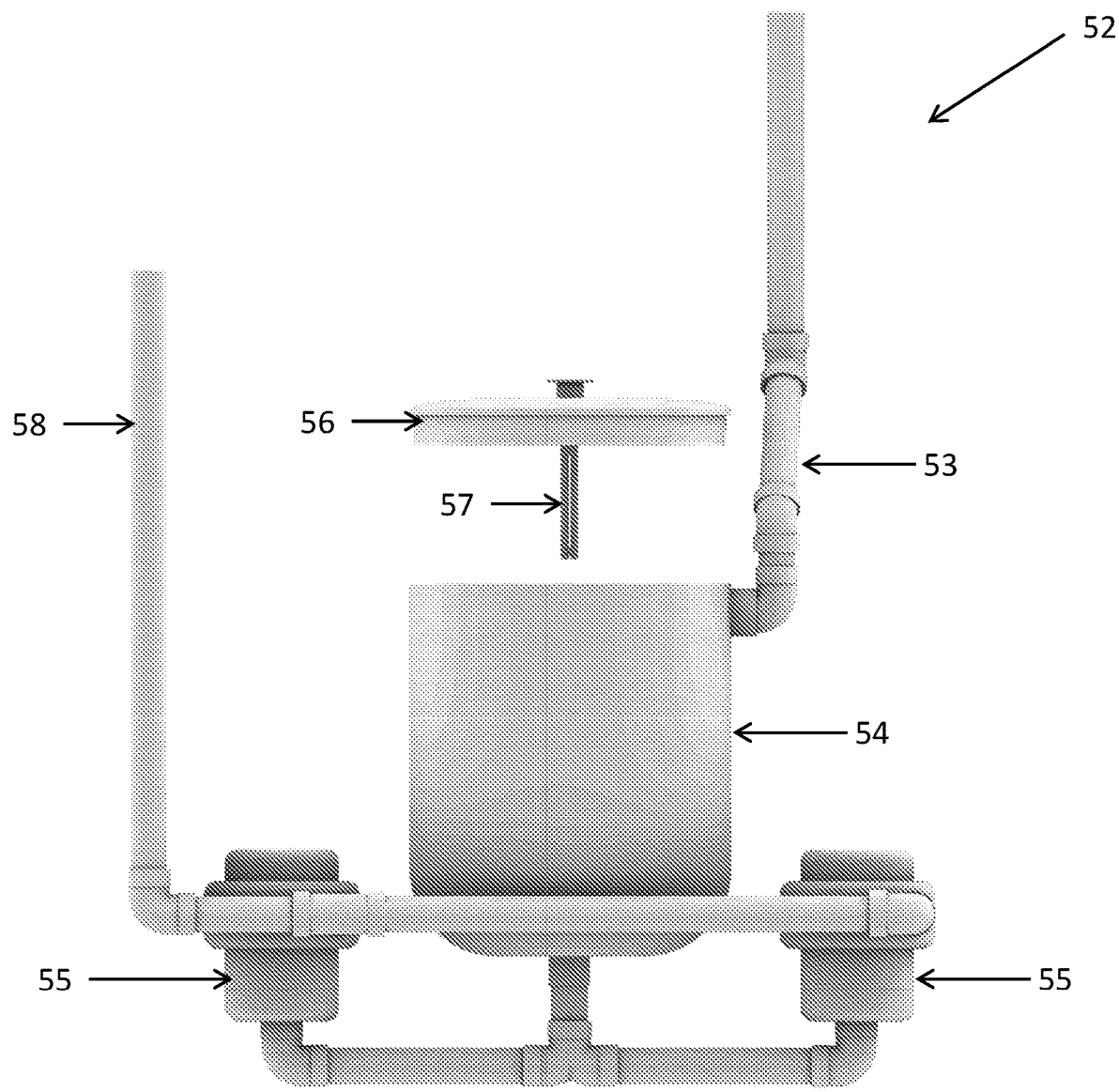
FIG. 12 shows the detail of the central vacuum assembly.

FIG. 12 identifies the components of the central vacuum unit 52 (in this embodiment CVS-219 DP CentralVac International, Dollar Bay, Mich.) which consists of the central vacuum collection canister 54 which collects debris fed by the central vacuum inlet 53 via vacuum generated by the vacuum motors 55 and treated by the central vacuum UVC/ozone bulb 57 attached to the underside of the central vacuum collection canister lid 56 before being ejected from the building through the externally vented vacuum exhaust 58.

Figure 13:
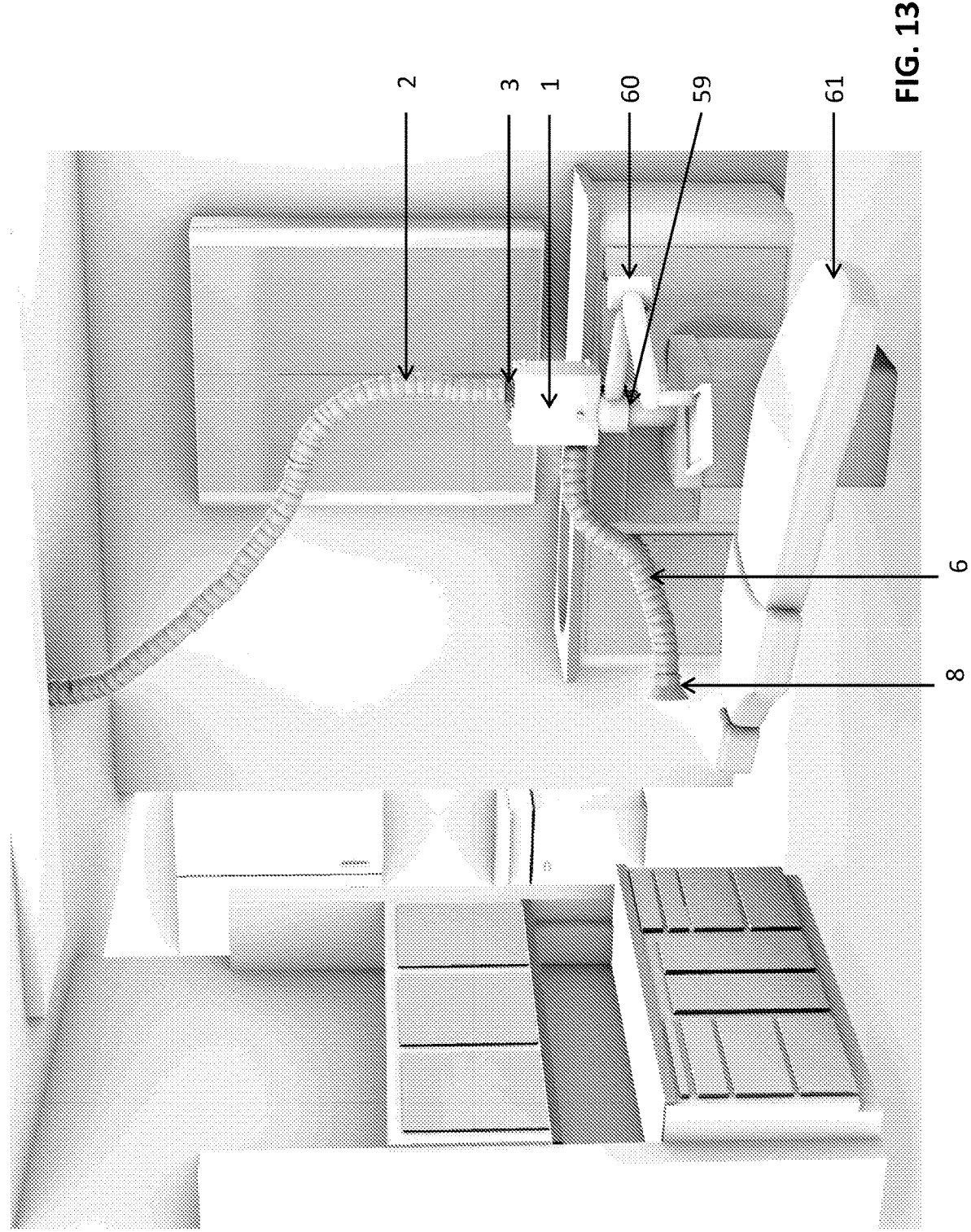
FIG. 13 shows the detail of the EVADE system installed in a typical dental treatment room.

FIG. 13 demonstrates installation in a typical dental treatment room setting. The ceiling mounted flexible vacuum tube 2 attaches to the EVADE filtration box 1 with the bulkhead mounted vacuum tube connector 3 and allows for positioning of the tube away from cabinetry, x-ray devices, ceiling lamps or any other objects in the treatment room. The EVADE filtration box 1 is mounted to the dental chair 61 by way of the dental chair post mounting assembly 90. The EVADE filtration box 1 remains in a fixed position because the U-channel at the end of the anti-rotational tube 14 engages a cross member pin inside the dental chair post 59 while the dental chair equipment delivery arm 60 rotates freely upon the chair post 59. The fixed position of EVADE filtration box 1 allows for stable positioning of the flexible aerosol collection tube 6 and the aerosol collection cone 8.

Figure 14:
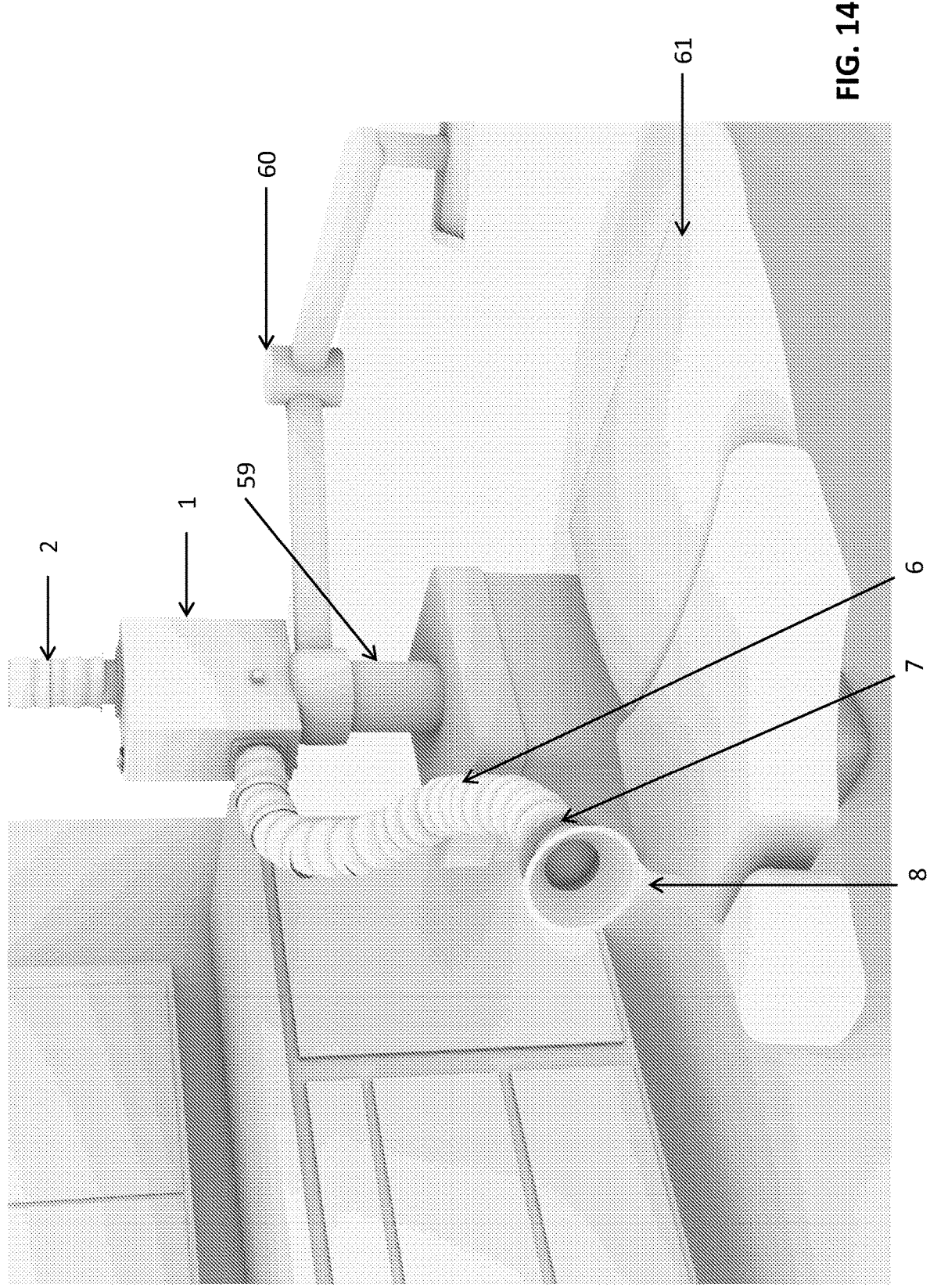
FIG. 14 shows the detail of the EVADE system mounted on a dental chair post.

FIG. 14 demonstrates a magnified view of a typical dental installation. The ceiling mounted flexible vacuum tube 2 attaches to the EVADE filtration box 1 mounted to the dental chair 61 by way of the dental chair post mounting assembly 90 detailed in FIG. 8. The EVADE filtration box 1 remains stationary because the U-channel at the end of the anti-rotational tube 14 detailed in FIG. 8 engages a cross member pin inside the dental chair post 59 while the dental chair equipment delivery arm 60 rotates freely upon the chair post 59. The fixed position of the EVADE filtration box 1 allows for stable positioning of the flexible aerosol collection tube 6 disposable aerosol collection filter 7 and the aerosol collection cone 8.

Figure 15:
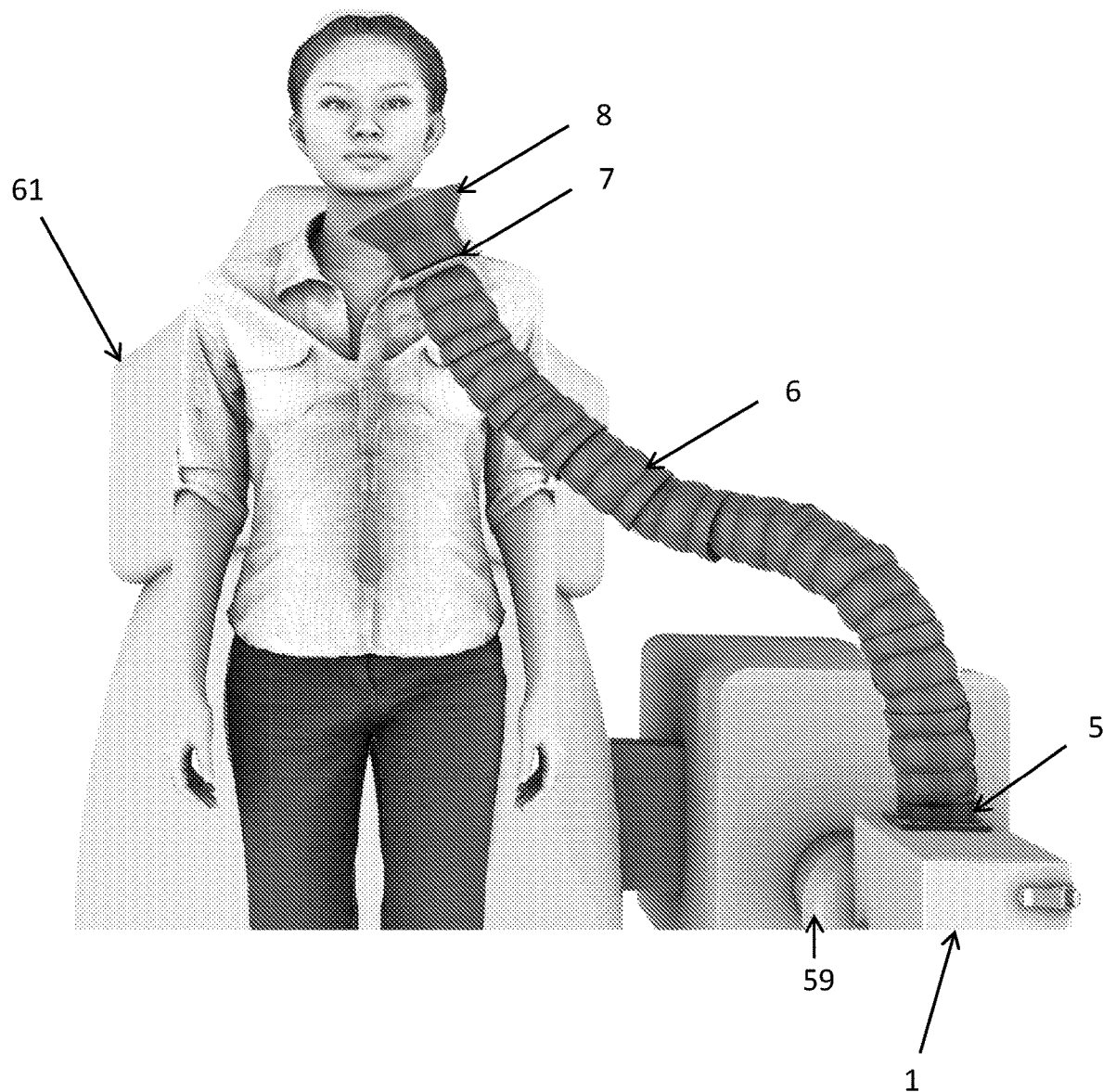
FIG. 15 shows the detail of the EVADE system collection hose positioning for patient use.

FIG. 15 demonstrates typical positioning of the EVADE filtration box 1 with the flexible aerosol collection tube 6 attached to the aerosol inlet bulkhead connector 5 for simple removal or replacement. The flexibility of the aerosol collection tube 6 allows the aerosol collection cone 8 with the disposable aerosol collection filter 7 to be placed in virtually any position relative to a patient in a dental chair 61.

USAGE OF THE INVENTION

The patient is seated and positioned for best access by the operator and the assistant. The EVADE System nozzle 8 is positioned above the patient's mouth and within 2-3 inches of the operative field so as to allow operator and assistant accessibility to the patient's mouth. The filter box 1 UVC/Ozone germicidal bulb 27, blast gate 32 and low voltage vacuum switch 38 are activated with the on/off button 9 or foot pedal remote 43 providing up to 280 CFM vacuum air flow at the nozzle.

The generated aerosol plume varies in intensity depending upon the instrumentation employed. Dental handpiece and ultrasonic scalers will generate more or less aerosol spray depending upon the speed and water flow used and the use and positioning of other traditional HVE (high volume evacuator) devices. The best position of the EVADE System cone for individual operators can be determined through experimentation scenarios. Aerosol capture can be tested with the room darkened and a light source trained on the aerosol plume from the assistant's side. The collection range of the aerosol plume can be easily observed and the nozzle position adjusted accordingly.

After use, the inside of the flex tubing 6 and pipe connection 5 to the filter box 1 is disinfected by a 10 second application of an appropriate germicidal spray while the vacuum is activated. The flex tube plastic barrier, nozzle filter 7 and the nozzle 8 are removed after use and disinfected using an appropriate agent, such as germicidal Lysol. The plastic barrier is replaced and the disposable filter 7 and nozzle 8 replaced/reattached. Filter box 1 maintenance consists of periodic replacement of the HEPA filters 23, replacement of the UVC/Ozone germicidal bulb 27.

While primarily shown and described in conjunction with dental aerosol collection applications, it is understood that embodiments can be directed to various other settings in which oral aerosols are created such a medical examinations, introduction of aerosol anesthetic agents during nasal surgery, nasopharyngeal examinations, nasal or oral swabbing for COVID or other diseases or any other procedures which may generate aerosols or patient coughing or sneezing. A disposable plastic barrier sleeve may be placed to cover the collection tube to aid in disinfection between uses.

While shown and described herein as an installation fixed directly to a dental chair, the system can be installed for any use and in any desired location that is accessible for maintenance such as a ceiling or countertop placement. It is preferable to minimize the length of potentially contaminated collection hose prior to filtration The description assembled here of various aspects of the invention has been presented for the purposes of illustration and description. Many modifications and variations are possible regarding the size, specific components and arrangement of those components for example. The descriptions and drawings included herein are not intended to limit the invention to the precise form demonstrated or to be exhaustive. Modifications and variations which may be apparent to an individual skilled in the art are included within the scope of the invention as defined by the accompanying claims.

The descriptions and illustrations herein are a preferred embodiment of the invention along with a discussion of some of its variations. The descriptions, terms, and figures used herein are provided for illustration only and are not meant as specific limitations. Many variations are possible within the spirit and scope of the invention and be this will be recognized by those skilled in the art. The specific products by others shown in this embodiment are not restrictive and may be substituted with other devices. The following claims (and their equivalents) are intended to be defined by their broadest reasonable sense unless otherwise indicated. There shall be no legal or limiting effect of any headings utilized within the description which are for convenience only.

I claim:

1. An aerosol collection and evacuation system comprising:
   1. a removable collection cone;
   2. a droplet pre-filter;
   3. a detachable flexible collection tube;
   4. a filtration box consisting of:
      a. a bulkhead inlet tubing adapter
      b. a UVC/Ozone germicidal bulb
      c. a mirrored disinfection chamber
      d. an anti-rotation post mounting assembly
      e. replaceable HEPA filtration
      f. an automated blast gate system
      g. an automated UVC bulb time delay apparatus
      h. a bulkhead outlet tubing adapter
      i. removable back cover with a gasket seal
   5. a wireless remote foot pedal;
   6. a flexible ceiling mounted vacuum tube;
   7. a ceiling mount; and
   8. a central vacuum collection system with external exhaust.

* * * * *